US009499489B2

(12) United States Patent
Plemper et al.

(10) Patent No.: US 9,499,489 B2
(45) Date of Patent: Nov. 22, 2016

(54) MYXOVIRUS THERAPEUTICS, COMPOUNDS, AND USES RELATED THERETO

(71) Applicants: Richard K. Plemper, Decatur, GA (US); James P. Snyder, Atlanta, GA (US); Aiming Sun, Atlanta, GA (US)

(72) Inventors: Richard K. Plemper, Decatur, GA (US); James P. Snyder, Atlanta, GA (US); Aiming Sun, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 14/352,176

(22) PCT Filed: Oct. 24, 2012

(86) PCT No.: PCT/US2012/061546
§ 371 (c)(1),
(2) Date: Apr. 16, 2014

(87) PCT Pub. No.: WO2013/063012
PCT Pub. Date: May 2, 2013

(65) Prior Publication Data
US 2014/0329817 A1    Nov. 6, 2014

Related U.S. Application Data

(60) Provisional application No. 61/550,674, filed on Oct. 24, 2011.

(51) Int. Cl.
*C07D 231/14* (2006.01)
*C07D 401/12* (2006.01)
(52) U.S. Cl.
CPC ........... *C07D 231/14* (2013.01); *C07D 401/12* (2013.01)
(58) Field of Classification Search
None
See application file for complete search history.

(56) References Cited

U.S. PATENT DOCUMENTS 8,729,059 B2    5/2014 Plemper
2014/0080828 A1    3/2014 Plemper

FOREIGN PATENT DOCUMENTS

EP        0199438        10/1986

OTHER PUBLICATIONS

Sun et al. Non-nuceloside inhibitros of the measles virus RNA-dependent RNA polymerase complex activity: Syntheis and in vitro evalutaion. Bioorganic and Medicinal Chemistry Letter 2007, 17, 5199-5203.*
Sun et al. Potent Non-Nucleoside Inhibitors of the Measles Virus RNA-Dependent RNA Polymerase Complex. Journal of Medicinal Chemistry 2008, 51, 3731-3741.*
Yoon et al. Target Analysis of the Experimental Measles Therapeutics AS-136A. Antimicrobial Agents and Chemotherapy 2009, 53, 3860-3870.*
Chemical Abstract Registry No. 1240901-54-5, indexed in the Registry File on STN CAS Online Sep. 14, 2010.*
Rasheed et al. Cyclodextrins as Drug Carrier Molecule: A Review. Scientia Pharmacetuica 2008, 76, 567-598.*
Plemper et al., Measles control—Can measles virus inhibitors make a difference?. Current Opinion on Investigational Drugs, 2009, 10, 811-820.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Yoon et al., High-Throughput Screening Based Identification of Paramyxovirus Inhibitors, J Biomol Screen, 2008; 13 (7): 591-608.
Plemper et al., Structural and mechanistic studies of measles virus illuminate paramyxovirus entry.PLoS Pathog. 2011, 7(6):e1002058.
Krumm et al. Potent Host-Directed Small-Molecule Inhibitors of Myxovirus RNA-Dependent RNA-Polymerases PLoS ONE, 2011, 6(5), e20069.
Ndungu et al., Non-nucleoside inhibitors of the measles virus RNA-dependent RNA polymerase: synthesis, structure-activity relationships, and pharmacokinetics, J Med Chem. 2012, 55(9):4220-30.
White, et al., 2007, Nonnucleoside inhibitors of measles virus RNA-dependent RNA polymerase complex activity, Antimicrobial Agents and Chemotherapy, 51(7):2293-2303.
Tonew et al. Inhibition of mengovirus RNA-dependent RNA polymerase by an isatinisothiosemicarbazone and a piperidine-thiocarbonyl-hydrazone derivative in a cell-free system, Virologie. Apr.-Jun. 1980;31(2):135-40.
Extended European Search Report for EP application No. 12844117.7 dated Mar. 24, 2015.

* cited by examiner

Primary Examiner — Rebecca Anderson
Assistant Examiner — Po-Chih Chen
(74) Attorney, Agent, or Firm — Emory Patent Group

(57) ABSTRACT

This disclosure relates to antiviral compounds disclosed herein and uses related thereto. In certain embodiments, the disclosure relates to pharmaceutical compositions. Typically, the pharmaceutical composition comprises a compound of formula I: Formula I, or salt, prodrug, or ester thereof wherein X, Y, and $R^1$ and $R^{10}$ to $R^{13}$ are described herein.

Formula I

4 Claims, 6 Drawing Sheets

MYXOVIRUS THERAPEUTICS, COMPOUNDS, AND USES RELATED THERETO

CROSS-REFERENCE TO RELATED APPLICATIONS

This application claims priority to U.S. Provisional Application No. 61/550,674 filed Oct. 24, 2011, hereby incorporated by reference in its entirety.

ACKNOWLEDGEMENTS

This invention was made with government support under Grants HG003918-02, AI085328, and AI071002 awarded by National Institutes of Health. The government has certain rights in the invention.

BACKGROUND

Myxoviruses, i.e., viruses in orthomyxoviridae and paramyxoviridae families, are RNA viruses. Influenza is in the orthomyxoviridae family. Influenza virus is the leading cause of morbidity and mortality from respiratory disease in North America despite the existence of vaccine prophylaxis. This is due to the fact that the vaccines currently in use reduce illness in approximately 70% of healthy adults when homologous to the prevalent circulating virus, but protection in the elderly reaches only approximately 40%. Vaccine efficacy is reduced substantially when the circulating strains differ from those constituting the vaccine.

Current influenza drugs have limited efficacy. For example, Oseltamivir (Tamiflu) is an antiviral drug that slows the spread of influenza virus. However, it has been reported that Tamiflu offered mild benefits in terms of duration of symptoms for healthy adults if taken within 24 hours of onset of symptoms, but there was no clear evidence it prevented lower respiratory tract infections or other complications of influenza. Thus, there is a need to identify improved methods for treating or preventing influenza infections.

Measles virus (MV), a representative of the paramyxovirus family, is one of the most infectious viruses identified. Despite enhanced efforts for global implementation of a live-attenuated vaccine, MV is a principle cause of morbidity, and infection results in approximately 300,000 to 400,000 deaths annually worldwide, rendering the virus the leading cause of childhood deaths from a vaccine-preventable disease globally. Low vaccination coverage in parts of the developing world and insufficient or declining herd immunity in several developed countries contribute to continued MV activity. In addition to a substantial immunosuppression that lasts several months, complications associated with MV infection include acute encephalitis and subacute sclerosing panencephalitis (SSPE), a late lethal sequela that manifests itself years after the primary infection. Currently, Ribavirin is the only drug approved for the treatment of some paramyxovirus infections. It has been used experimentally against MV but with limited efficacy. Thus, there is a need to identify additional agents to treat or prevent MV.

Yoon et al., J Biomol Screen., 2008, 13(7): 591-608 disclose a high-throughput screening protocol that permits screening against non-attenuated wild type MV strains and identified a panel of candidates.

SUMMARY

This disclosure relates to antiviral compounds disclosed herein and uses related thereto. In certain embodiments, the disclosure relates to pharmaceutical compositions. Typically, the pharmaceutical composition comprises a compound of formula I:

$$\text{Formula I}$$

or salt, prodrug, or ester thereof wherein X, Y, and $R^1$ and $R^{10}$ to $R^{13}$ along with other embodiments are described herein.

Further, the pharmaceutical compositions may comprise the compound as a pharmaceutically acceptable salt in combination with a pharmaceutically acceptable excipient such as a dilutant, carrier, filler, or buffer.

The pharmaceutical composition may further comprise dimethacrylated cyclodextrin and optionally polyethylene glycol.

The excipient may be, but is not limited to, an anti-adherent such as magnesium stearate, a binder such as a sugar, saccharide, or cellulose, a coating such as hydroxypropyl methylcellulose and gelatin, a disintegrant such as crospovidone and croscarmellose sodium, a filler such as water, salts, sugars, celluloses, calcium phosphates, fats, and oils, a lubricant such as talc, silica, fats, and magnesium stearate.

In certain embodiments, the disclosure relates to uses of compounds disclosed herein in the production of a medicament for the treatment or prevention of a pathogenic infection.

In certain embodiments, the disclosure relates to methods of treating a pathogenic infection. The methods may comprise administering a pharmaceutical composition as provided herein to a subject at risk of, exhibiting symptoms of, suspected of, or diagnosed with a viral infection. In certain embodiments the virus is an RNA virus or a DNA virus that replicates through an RNA intermediate. In certain embodiments, the RNA virus is a positive, negative sense, or ambisense single stranded virus. In certain embodiments, the RNA virus is double stranded. In certain embodiments, the RNA virus is a retrovirus. RNA viruses contemplated include human parainfluenza viruses, influenza A virus including subtype H1N1, influenza B virus, influenza C virus, rotavirus A, rotavirus B, rotavirus C, rotavirus D, rotavirus E, human metapneumovirus, SARS coronavirus, parvovirus B19, hepatitis A, hepatitis C, hepatitis E, yellow fever virus, measles virus, mumps virus, respiratory syncytial virus, norovirus, west nile virus, dengue virus, rubella virus, rabies virus, ebola virus, and marburg virus, distemper virus, rinderpest virus, and Nipah and Hendra viruses.

In certain embodiments, the subject is diagnosed with JC virus (JCV), BK virus, Merkel cell polyomavirus, coxsackie A virus, lymphocytic choriomeningitis virus (LCMV), rinderpest virus, California encephalitis virus, hantavirus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis B, hepatitis D, or human immunodeficiency virus (HIV).

In certain embodiments, RNA tick-borne viruses are contemplated such as those in the families: Asfarviridae, Reoviridae, Rhabdoviridae, Orthomyxoviridae, Bunyaviridae, Flaviviridae. Exemplary tick-borne viruses include tick-borne encephalitis virus, Crimean-Congo haemorrhagic fever virus, African swine fever virus, Nairobi sheep disease virus, Banna virus, Tahyna virus, louping ill virus, Powassan virus, Kyasanur Forest disease virus, and Omsk hemorrhagic fever virus.

In certain embodiments, the pharmaceutical composition is administered in combination with one or more additional/second antiviral agent(s).

In certain embodiments, the disclosure relates to methods of preparing compounds disclosed herein by mixing the starting materials under conditions disclosed herein to form the products.

DETAILED DISCUSSION

Structure-activity relationship (SAR) studies around a pyrazole carboxamide scaffold led to the discovery of AS-136a a blocker with potency in the MeV virus titer reduction assay and attractive physical properties suitable for therapeutic development. However, it has limited water solubility and oral bioavailability (F) in the rat. Thus, it is desirable to identify improved pharmaceutical products.

Figure 1:
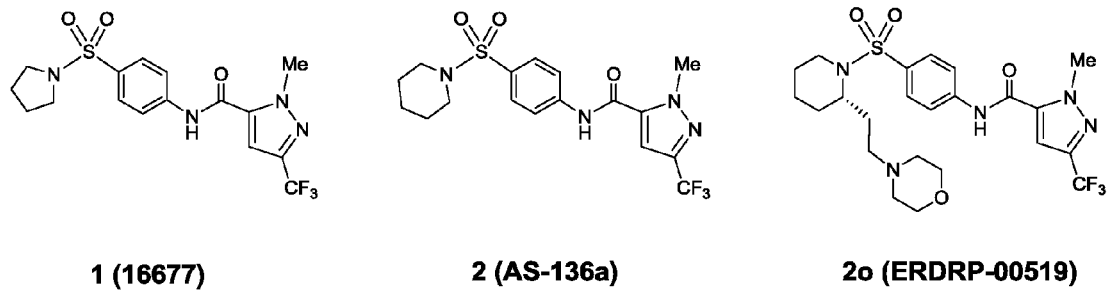
FIG. 1 illustrates certain embodiments of the disclosure.

A structure-activity relationship (SAR) strategy led to the discovery of additional compounds disclosed herein. ERDRP-00519 (also designated 20) is an inhibitor of MeV with aqueous solubility around 60 g/ml (See FIG. 1). The agent shows a 10-fold exposure (AUC/Cmax) increase in rat relative to AS-136a and displays near dose proportionality in the range of 10 mg/kg to 50 mg/kg. The significant solubility increase appears to contribute to the improvement in oral bioavailability (F). Compound 2o was further investigated, and a pharmacokinetic comparison of AS-136a, 2k and 2o are provided herein.

Compounds

In certain embodiments, the disclosure relates to compounds of Formula I:

Formula I prodrugs, esters, or salts thereof wherein,

X is O, S, NH, or $CH_2$;

Y is $SO_2$ or SO;

$R^1$ is dialkylamino, carbocyclyl, aryl, heterocyclyl, or heterocarbocyclyl optionally substituted with one or more, the same or different, $R^{14}$;

$R^{12}$ is heterocyclyl optionally substituted with one or more, the same or different, $R^{14}$;

$R^{10}$, $R^{11}$, and $R^{13}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^{10}$, $R^{11}$, and $R^{13}$ are optionally substituted with one or more, the same or different, $R^{14}$;

$R^{14}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is 2-ethyl-piperidin-1-yl or 2-ethyl-1-ene-piperidin-1-yl further substituted with one or more, the same or different, $R^{15}$.

In certain embodiments, $R^1$ is 2-hydoxymethyl-piperidin-1-yl further substituted with one or more, the same or different, $R^{15}$.

In certain embodiments, $R^1$ is 2-methyl-pyrrolidin-1-yl optionally substituted with one or more, the same or different, $R^{15}$.

In certain embodiments, $R^1$ is pyrrolidinyl or piperidinyl further substituted with $R^{14}$, wherein $R^{14}$ is ethyl, hydroxymethyl, 2-hydroxyethyl, or 3-hydroxypropyl, wherein $R^{14}$ is further substituted with one or more, the same or different, $R^{15}$.

In certain embodiments, $R^1$ is pyrrolidinyl or piperidinyl further substituted $R^{14}$, wherein $R^{14}$ is 2-hydroxyethyl or 3-hydroxypropyl, wherein $R^{14}$ optionally substituted with one or more, the same or different, $R^{15}$.

In certain embodiments $R^1$ is methylamino further substituted with $C_{2-6}$alkyl or higher alkyl optionally substituted with one or more, the same or different, $R^{14}$.

In certain embodiments, $R^1$ is azetidinyl or aziridinyl wherein $R^1$ is optionally substituted with one or more, the same or different, $R^{14}$.

In certain embodiments, $R^1$ is phenyl optionally substituted with one or more, the same or different, $R^{14}$.

In certain embodiments, $R^{12}$ is pyrazolyl optionally substituted with one or more, the same or different, $R^{14}$.

In certain embodiments, $R^{12}$ is 1,3-dimethyl-pyrazol-5-yl optionally substituted with one or more, the same or different, halogen.

In certain embodiments, X is NH and Y is $SO_2$.

In certain embodiments, $R^{10}$, $R^{11}$, and $R^{13}$ are hydrogen.

In certain embodiments, the disclosure relates to compounds of Formula IA:

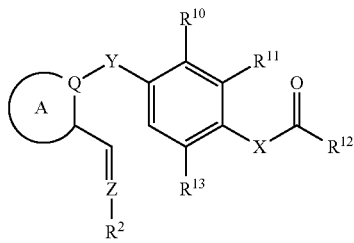

Formula IA prodrugs, esters, or salts thereof wherein,
the dotted line is a double or single bond;
A is an aryl, heterocarbocyclyl, or heterocyclyl wherein the A ring is optionally substituted with one or more, the same or different, $R^{14}$;
Q is C or N;
X is O, S, NH, or $CH_2$;
Y is $SO_2$ or SO;
Z is O, S, N, NH, CH, or $CH_2$,
$R^2$ is alkyl, hydroxy, alkoxy, alkanoyl, or heterocarbocyclyl optionally substituted with one or more $R^{14}$;
$R^{12}$ is heterocyclyl optionally substituted with one or more, the same or different, $R^{14}$;
$R^{10}$, $R^{11}$, and $R^{13}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^{10}$, $R^{11}$, and $R^{13}$ are optionally substituted with one or more, the same or different, $R^{14}$;

$R^{14}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the Q is N and A is a 3 to 6 membered heterocyclic ring optionally substituted with one or more, the same or different, $R^{14}$.

In certain embodiments, Y is $SO_2$, and X is NH, Z is O or methylene, and the dotted line is a single bond.

In certain embodiments, $R^{12}$ is pyrazolyl optionally substituted with one or more, the same or different, $R^{14}$.

In certain embodiments, $R^{12}$ is 1,3-dimethyl-pyrazol-5-yl optionally substituted with one or more, the same or different, halogen.

In certain embodiments, X is NH and Y is $SO_2$.

In certain embodiments, $R^{10}$, $R^{11}$, and $R^{13}$ are hydrogen.

In certain embodiments, the disclosure relates to compounds of Formula IB:

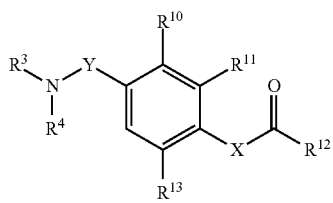

Formula IB prodrugs, esters, or salts thereof wherein,
X is O, S, NH, or $CH_2$;
Y is $SO_2$ or SO;
$R^3$ is hydrogen or methyl;
$R^4$ is alkyl optionally substituted with one or more, the same or different, $R^{14}$ provided $R^4$ is not methyl;
$R^{12}$ is heterocyclyl optionally substituted with one or more, the same or different, $R^{14}$;
$R^{10}$, $R^{11}$, and $R^{13}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^{10}$, $R^{11}$, and $R^{13}$ are optionally substituted with one or more, the same or different, $R^{14}$;

$R^{14}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ is pyrazolyl optionally substituted with one or more, the same or different, $R^{14}$.

In certain embodiments, $R^{12}$ is 1,3-dimethyl-pyrazol-5-yl optionally substituted with one or more, the same or different, halogen.

In certain embodiments, X is NH and Y is SO$_2$.

In certain embodiments, $R^{10}$, $R^{11}$, and $R^{13}$ are hydrogen.

In certain embodiments, the disclosure relates to compounds of Formula IC:

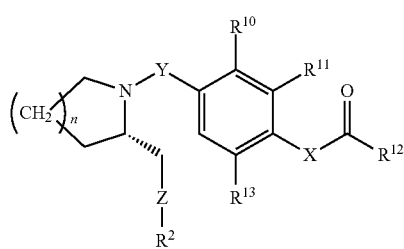

Formula IC prodrugs, esters, or salts thereof wherein,
n is 1 or 2;
X is O, S, NH, or CH$_2$;
Y is SO$_2$ or SO;
Z is O, S, N, NH, CH, or CH$_2$,
$R^2$ is alkyl, hydroxy, alkoxy, alkanoyl, or heterocarbocyclyl optionally substituted with one or more $R^{14}$;
$R^{12}$ is heterocyclyl optionally substituted with one or more, the same or different, $R^{14}$;
$R^{10}$, $R^{11}$, and $R^{13}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^{10}$, $R^{11}$, and $R^{13}$ are optionally substituted with one or more, the same or different, $R^{14}$;

$R^{14}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Z may be additionally be hydrogen.

In certain embodiments, the compound of Formula IC is in a composition with greater than 55%, 60%, 70%, 80%, 90% enantiomeric or diastereomeric excess.

In certain embodiments, $R^{12}$ is pyrazolyl optionally substituted with one or more, the same or different, $R^{14}$.

In certain embodiments, $R^{12}$ is 1,3-dimethyl-pyrazol-5-yl optionally substituted with one or more, the same or different, halogen.

In certain embodiments, X is NH and Y is SO$_2$.

In certain embodiments, $R^{10}$, $R^{11}$, and $R^{13}$ are hydrogen.

In certain embodiments, the disclosure relates to compounds of Formula ID

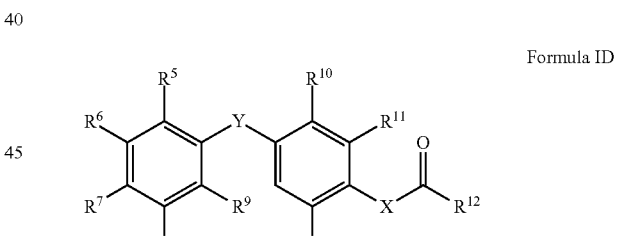

Formula ID prodrugs, esters, or salts thereof wherein,
X is O, S, NH, or CH$_2$;
Y is SO$_2$ or SO;
$R^5$, $R^6$, $R^7$, $R^8$, and $R^9$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^5$, $R^6$, $R^7$, $R^8$, and $R^9$ are optionally substituted with one or more, the same or different, $R^{14}$;

$R^{12}$ is heterocyclyl optionally substituted with one or more, the same or different, $R^{14}$;

$R^{10}$, $R^{11}$, and $R^{13}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^{10}$, $R^{11}$, and $R^{13}$ are optionally substituted with one or more, the same or different, $R^{14}$;

$R^{14}$ is alkyl, halogen, nitro, cyano, hydroxy, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ is pyrazolyl optionally substituted with one or more, the same or different, $R^{14}$.

In certain embodiments, $R^{12}$ is 1,3-dimethyl-pyrazol-5-yl optionally substituted with one or more, the same or different, halogen.

In certain embodiments, X is NH and Y is SO$_2$.

In certain embodiments, $R^{10}$, $R^{11}$, and $R^{13}$ are hydrogen.

In certain embodiments, the compound of Formula I is selected from:

1-methyl-N-(4-(piperidin-1-ylsulfonyl)phenyl)-3-(trifluoromethyl)-pyrazole-5-carboxamide;
N-(4-((2-(2-hydroxyethyl)piperidin-1-yl)sulfonyl)phenyl)-1-methyl-3-(trifluoromethyl)-pyrazole-5-carboxamide;
1-methyl-N-(4-((2-(2-morpholinoethyl)piperidin-1-yl)sulfonyl)phenyl)-3-(trifluoromethyl)-pyrazole-5-carboxamide;
1-methyl-N-(4-(phenylsulfonyl)phenyl)-3-(trifluoromethyl)-pyrazole-5-carboxamide;
ethyl 3-(1-((4-(1-methyl-3-(trifluoromethyl)-pyrazole-5-carboxamido)phenyl)sulfonyl)piperidin-2-yl)acrylate;
ethyl 3-(1-((4-(1-methyl-3-(trifluoromethyl)-pyrazole-5-carboxamido)phenyl)sulfonyl)piperidin-2-yl)propanoate;
3-(1-((4-(1-methyl-3-(trifluoromethyl)-pyrazole-5-carboxamido)phenyl)sulfonyl)piperidin-2-yl)propanoic acid;
3-(1-((4-(1-methyl-3-(trifluoromethyl)-pyrazole-5-carboxamido)phenyl)sulfonyl)piperidin-2-yl)acrylic acid;
N-(4-((2-(3-hydroxypropyl-1-ene)piperidin-1-yl)sulfonyl)phenyl)-1-methyl-3-(trifluoromethyl)-pyrazole-5-carboxamide;
N-(4-((2-(3-hydroxypropyl)piperidin-1-yl)sulfonyl)phenyl)-1-methyl-3-(trifluoromethyl)-pyrazole-5-carboxamide;
N-(4-((2-(2-azidoethyl)piperidin-1-yl)sulfonyl)phenyl)-1-methyl-3-(trifluoromethyl)-pyrazole-5-carboxamide;
ethyl 2-((1-((4-(1-methyl-3-(trifluoromethyl)-pyrazole-5-carboxamido)phenyl)sulfonyl)piperidin-2-yl)methoxy)acetate;
2-((1-((4-(1-methyl-3-(trifluoromethyl)-pyrazole-5-carboxamido)phenyl)sulfonyl)piperidin-2-yl)methoxy)acetic acid;
N-(4-((2-((2-hydroxyethoxy)methyl)piperidin-1-yl)sulfonyl)phenyl)-1-methyl-3-(trifluoromethyl)-pyrazole-5-carboxamide;
N-(4-((2-((2-methoxyethoxy)methyl)piperidin-1-yl)sulfonyl)phenyl)-1-methyl-3-(trifluoromethyl)-pyrazole-5-carboxamide;
N-(4-((2-(methoxymethyl)piperidin-1-yl)sulfonyl)phenyl)-1-methyl-3-(trifluoromethyl)-pyrazole-5-carboxamide;
1-methyl-N-(4-((2-(methyl(2-morpholinoethyl)amino)piperidin-1-yl)sulfonyl)phenyl)-3-(trifluoromethyl)-pyrazole-5-carboxamide;
N-(4-((2-(ethyl(2-morpholinoethyl)amino)piperidin-1-yl)sulfonyl)phenyl)-1-methyl-3-(trifluoromethyl)-pyrazole-5-carboxamide;
N-(4-((2-(isobutyl(2-morpholinoethyl)amino)piperidin-1-yl)sulfonyl)phenyl)-1-methyl-3-(trifluoromethyl)-pyrazole-5-carboxamide;
N-(4-((2-(allyl(2-morpholinoethyl)amino)piperidin-1-yl)sulfonyl)phenyl)-1-methyl-3-(trifluoromethyl)-pyrazole-5-carboxamide;
N-(4-((2-((2-hydroxyethyl)(methyl)amino)piperidin-1-yl)sulfonyl)phenyl)-1-methyl-3-(trifluoromethyl)-pyrazole-5-carboxamide;
1-methyl-N-(4-((2-(2-methylaziridin-1-yl)piperidin-1-yl)sulfonyl)phenyl)-3-(trifluoromethyl)-pyrazole-5-carboxamide;
N-(4-((2-(ethyl(methyl)amino)piperidin-1-yl)sulfonyl)phenyl)-1-methyl-3-(trifluoromethyl)-pyrazole-5-carboxamide;
N-(4-((2-(isobutyl(methyl)amino)piperidin-1-yl)sulfonyl)phenyl)-1-methyl-3-(trifluoromethyl)-pyrazole-5-carboxamide;
N-(4-((2-(tert-butyl(methyl)amino)piperidin-1-yl)sulfonyl)phenyl)-1-methyl-3-(trifluoromethyl)-pyrazole-5-carboxamide;
1-methyl-3-(trifluoromethyl)-N-(4-((2-vinylpiperidin-1-yl)sulfonyl)phenyl)-pyrazole-5-carboxamide;
N-(4-((2-((methoxymethoxy)methyl)piperidin-1-yl)sulfonyl)phenyl)-1-methyl-3-(trifluoromethyl)-pyrazole-5-carboxamide;
N-(4-((2-(aminomethyl)piperidin-1-yl)sulfonyl)phenyl)-1-methyl-3-(trifluoromethyl)-pyrazole-5-carboxamide;
N-(4-((2-(acetamidomethyl)piperidin-1-yl)sulfonyl)phenyl)-1-methyl-3-(trifluoromethyl)-pyrazole-5-carboxamide;
N-(4-((2-((dimethylamino)methyl)piperidin-1-yl)sulfonyl)phenyl)-1-methyl-3-(trifluoromethyl)-pyrazole-5-carboxamide;
N-(4-((2-(3-aminopropyl)piperidin-1-yl)sulfonyl)phenyl)-1-methyl-3-(trifluoromethyl)-pyrazole-5-carboxamide;
1-methyl-N-(4-((2-(morpholinomethyl)piperidin-1-yl)sulfonyl)phenyl)-3-(trifluoromethyl)-pyrazole-5-carboxamide;
N-(4-((2-(benzyl(2-morpholinoethyl)amino)piperidin-1-yl)sulfonyl)phenyl)-1-methyl-3-(trifluoromethyl)-pyrazole-5-carboxamide;
1-methyl-N-(4-((2-((2-methylallyl)(2-morpholinoethyl)amino)piperidin-1-yl)sulfonyl)phenyl)-3-(trifluoromethyl)-pyrazole-5-carboxamide;
N-(4-((2-((2-(dimethylamino)ethyl)(methyl)amino)piperidin-1-yl)sulfonyl)phenyl)-1-methyl-3-(trifluoromethyl)-pyrazole-5-carboxamide;
N-(4-((2-(azetidin-1-yl)piperidin-1-yl)sulfonyl)phenyl)-1-methyl-3-(trifluoromethyl)-pyrazole-5-carboxamide;
methyl 2-(methyl(1-((4-(1-methyl-3-(trifluoromethyl)-pyrazole-5-carboxamido)phenyl)sulfonyl)piperidin-2-yl)amino)acetate;

1-methyl-N-(4-((2-(2-(4-methylpiperazin-1-yl)ethyl)piperidin-1-yl)sulfonyl)phenyl)-3-(trifluoromethyl)-pyrazole-5-carboxamide;

N-(4-((3-((methoxymethoxy)methyl)piperidin-1-yl)sulfonyl)phenyl)-1-methyl-3-(trifluoromethyl)-pyrazole-5-carboxamide;

N-(4-((4-((methoxymethoxy)methyl)piperidin-1-yl)sulfonyl)phenyl)-1-methyl-3-(trifluoromethyl)-pyrazole-5-carboxamide;

N-(4-((2-((methoxymethoxy)methyl)pyrrolidin-1-yl)sulfonyl)phenyl)-1-methyl-3-(trifluoromethyl)-pyrazole-5-carboxamide;

N-(4-(benzylsulfonyl)phenyl)-1-methyl-3-(trifluoromethyl)-pyrazole-5-carboxamide;

N-(4-((2-bromophenyl)sulfonyl)phenyl)-1-methyl-3-(trifluoromethyl)-pyrazole-5-carboxamide;

1-methyl-N-(4-((2-nitrophenyl)sulfonyl)phenyl)-3-(trifluoromethyl)-pyrazole-5-carboxamide;

N-(4-((2-methoxyphenyl)sulfonyl)phenyl)-1-methyl-3-(trifluoromethyl)-pyrazole-5-carboxamide;

1-methyl-N-(4-((2-(morpholinomethyl)phenyl)sulfonyl)phenyl)-3-(trifluoromethyl)-pyrazole-5-carboxamide;

N-(4-((2-hydroxyphenyl)sulfonyl)phenyl)-1-methyl-3-(trifluoromethyl)-pyrazole-5-carboxamide;

N-(4-((2-aminophenyl)sulfonyl)phenyl)-1-methyl-3-(trifluoromethyl)-pyrazole-5-carboxamide;

1-methyl-N-(4-((2-(2-morpholinoethyl)phenyl)sulfonyl)phenyl)-3-(trifluoromethyl)-pyrazole-5-carboxamide;

N-(4-((2-azidophenyl)sulfonyl)phenyl)-1-methyl-3-(trifluoromethyl)-pyrazole-5-carboxamide;

2-((4-(1-methyl-3-(trifluoromethyl)-pyrazole-5-carboxamido)phenyl)sulfonyl)phenyl acetate;

N-(4-((2-(1,2-dihydroxyethyl)phenyl)sulfonyl)phenyl)-1-methyl-3-(trifluoromethyl)-pyrazole-5-carboxamide;

N-(4-((2-(hydroxymethyl)phenyl)sulfonyl)phenyl)-1-methyl-3-(trifluoromethyl)-pyrazole-5-carboxamide;

1-methyl-N-(4-((2-(methyl(phenyl)amino)phenyl)sulfonyl)phenyl)-3-(trifluoromethyl)-pyrazole-5-carboxamide;

1-methyl-N-(4-((2-(phenylamino)phenyl)sulfonyl)phenyl)-3-(trifluoromethyl)-pyrazole-5-carboxamide; and N-(4-((2-(benzyl(methyl)amino)phenyl)sulfonyl)phenyl)-1-methyl-3-(trifluoromethyl)-pyrazole-5-carboxamide;

including prodrugs, esters, and salts thereof.

Terms

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, $-NR_aR_b$, $-NR_aC(=O)R_b$, $-NR_aC(=O)NR_aNR_b$, $-NR_aC(=O)OR_b$, $-NR_aSO_2R_b$, $-C(=O)R_a$, $-C(=O)OR_a$, $-C(=O)NR_aR_b$, $-OC(=O)NR_aR_b$, $-OR_a$, $-SR_a$, $-SOR_a$, $-S(=O)_2R_a$, $-OS(=O)_2R_a$ and $-S(=O)_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

An unspecified "R" group may be a hydrogen, lower alkyl, or aryl all of which may be optionally substituted with one or more substituents. Throughout the specification, groups and substituents thereof may be chosen to provide stable moieties and compounds.

Synthetic Preparation

Figure 2:
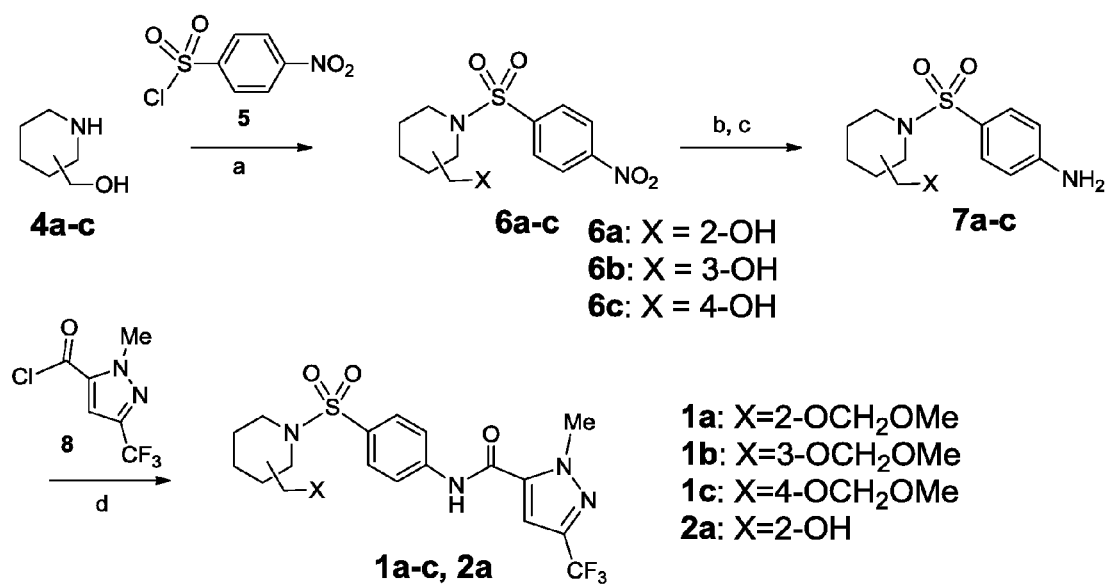
FIG. 2 illustrates preparation of embodiments of the disclosure. (a) $Na_2CO_3$, acetone; b) MOMCl, i-$Pr_2NEt$, $CH_2Cl_2$; c) $SnCl_2$, EtOAc; d) Pyridine, $CH_2Cl_2$.

The preparation of certain compounds described herein are provided for in the experimental section and outlined in FIGS. 2-6. Linkers were installed at the 2-, 3- and 4-positions of the pyrrolidine ring to explore which position could best accommodate hydrophilic substituents while maintaining potency. Reaction of different amino alcohols (4a-c) with 4-nitrobenzene sulfonyl chloride (5) followed by formation of MOM ethers and reduction of the nitro group afforded anilines 7a-c. Coupling of acid chloride 8, derived from 3-trifluoromethyl pyrazole using the method of Lahm, with anilines 7a-c provided analogs 1a-c (FIG. 2). Analogs of 2-piperidine methanol compound 2a were prepared by a sequence similar to that depicted in FIG. 2.

Figure 3:
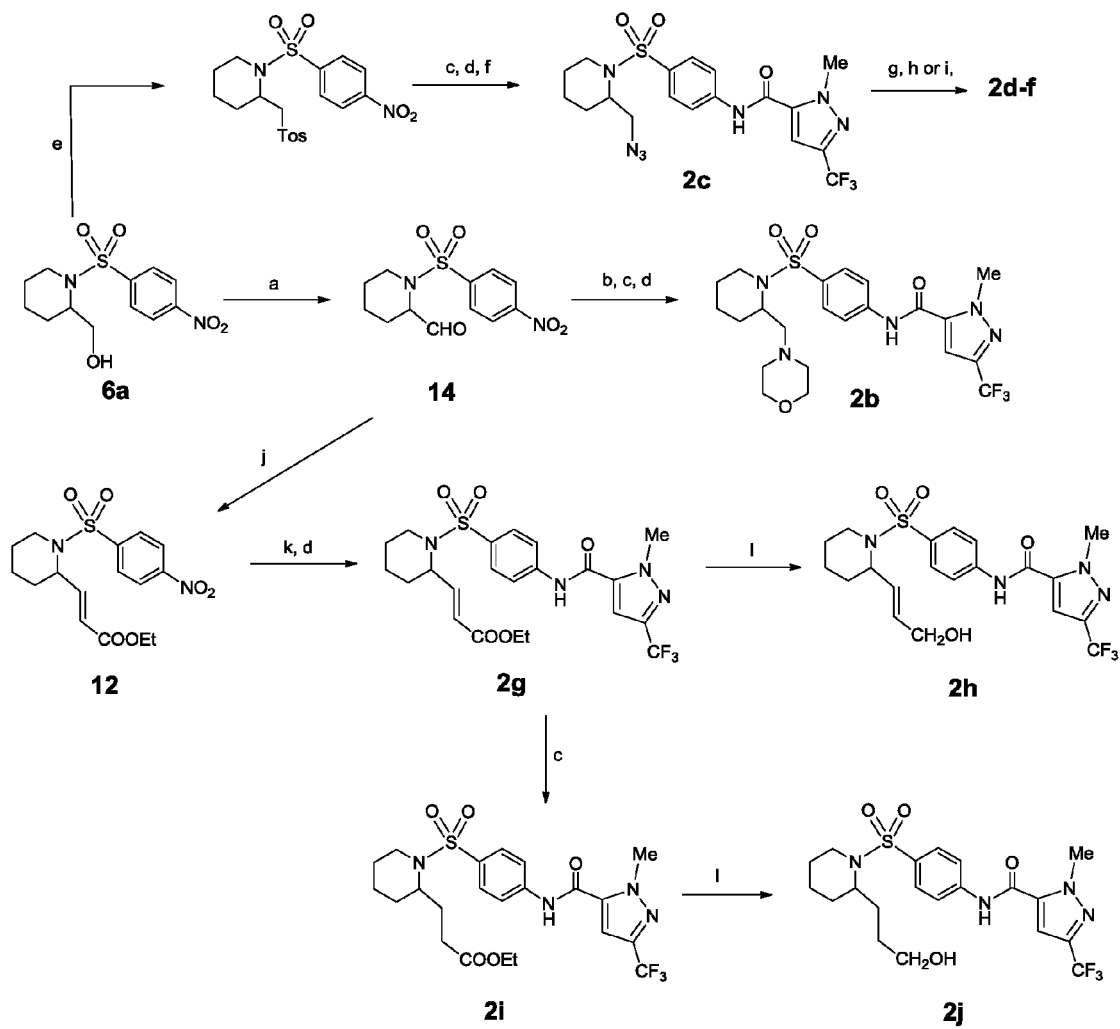
FIG. 3 illustrates preparation of embodiments of the disclosure. (a) PCC, $CH_2Cl_2$; (b) morpholine, $NaBH(OAc)_3$, $CH_2Cl_2$; (c) $H_2$, Pd/C, MeOH; (d) 8, i$Pr_2NEt$, CH2Cl2; (e) Tosyl chloride, $CH_2Cl_2$; (f) $NaN_3$, DMSO; (g) $SnCl_2$, EtOAc; (h) AcCl, $CH_2Cl_2$; (i) MeI, DMF; (j)) tBuOH, triethylphosphonate, THF; (k) $SnCl_2$, EtOAc; (l) DIBAL-H, THF.

Further analogs were prepared by PCC oxidation of 6a to obtain aldehyde 14, which was subjected to reductive amination with morpholine followed by the procedures illustrated in FIG. 3 to ultimately give analog 2b. Tosylation of 6a, reduction of the nitro group, coupling with acid chloride 8 and displacement of the tosylate with an azide furnished 2c. Reduction of the azide, dimethylation of the resultant amine or acylation resulted in compounds 2d-f. Further extension of the side chain including both saturated and unsaturated derivatives could be achieved from aldehyde 14. Homer-Wadsworth-Emmons olefination of 14 gave aniline 12. Union of 12 with acid chloride 8 afforded analog 2g, which was then reduced with DIBAL-H to obtain analog 2h. Hydrogenation of 2g delivered the saturated analog 2i, which was converted to 2j by treatment with DIBAL-H (FIG. 3).

Figure 4:
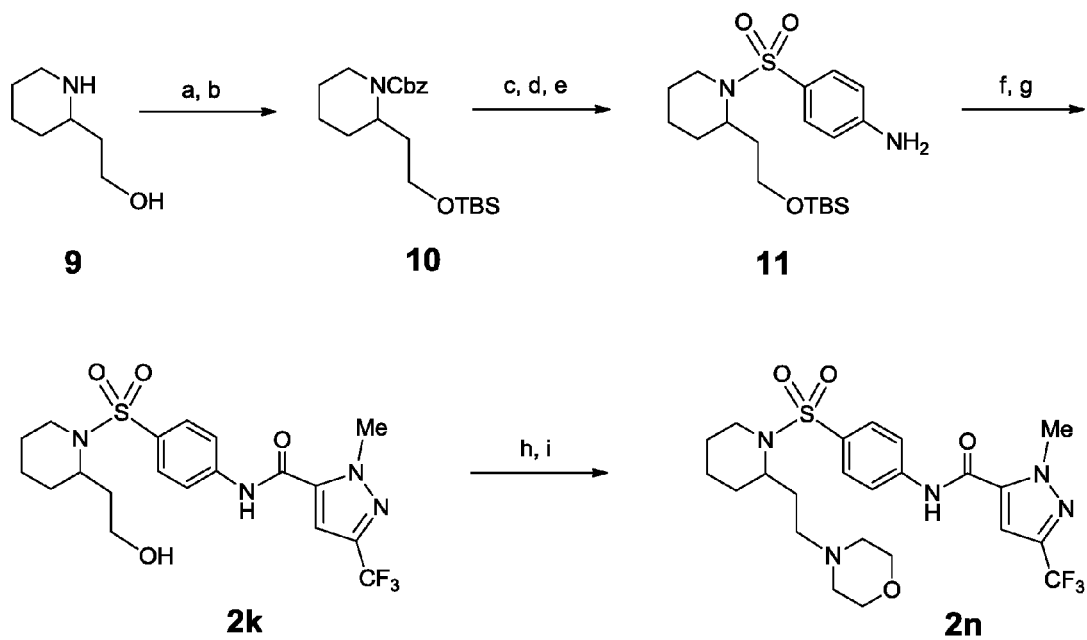
FIG. 4 illustrates preparation of embodiments of the disclosure. (a) $Na_2CO_3$, BzOCOCl, H2O/acetone; (b) TBSCl, imidazole, DMF; (c) $H_2$, Pd/C, ethanol; (d) 5, i$Pr_2NEt$, $CH_2Cl_2$; (e) $H_2$, Pd/C, ethanol, 40 psi; (f) 8, i$Pr_2NEt$, $CH_2Cl_2$; (g) TBAF, THF; (h) $(COCl)_2$, DMSO, $CH_2Cl_2$; (i) morpholine, $NaBH(OAc)_3$, $CH_2Cl_2$.

Preparation of two-carbon side chain analogs was accomplished by utilizing 2-piperidine ethanol 9. Direct coupling of the latter with p-nitro-benzenesulfonyl chloride 5 gave low yields of the desired product due to further coupling of the product with the sulfonyl chloride. To circumvent this shortcoming, NH— and OH— group of 9 was protected using benzyl chloroformate and TBSCl respectively. Deprotection of the amine, coupling with 5 and reduction of the nitro group afforded aniline 11. Coupling of 11 with acid chloride 8 followed by cleavage of the silyl group afforded alcohol 2k which, when subjected to Swern oxidation and reductive amination with morpholine, gave 2n (FIG. 4). Chiral pure enantiomer 2o was then prepared similar to 2n starting from (S)-2-piperidine ethanol.

Figure 5:
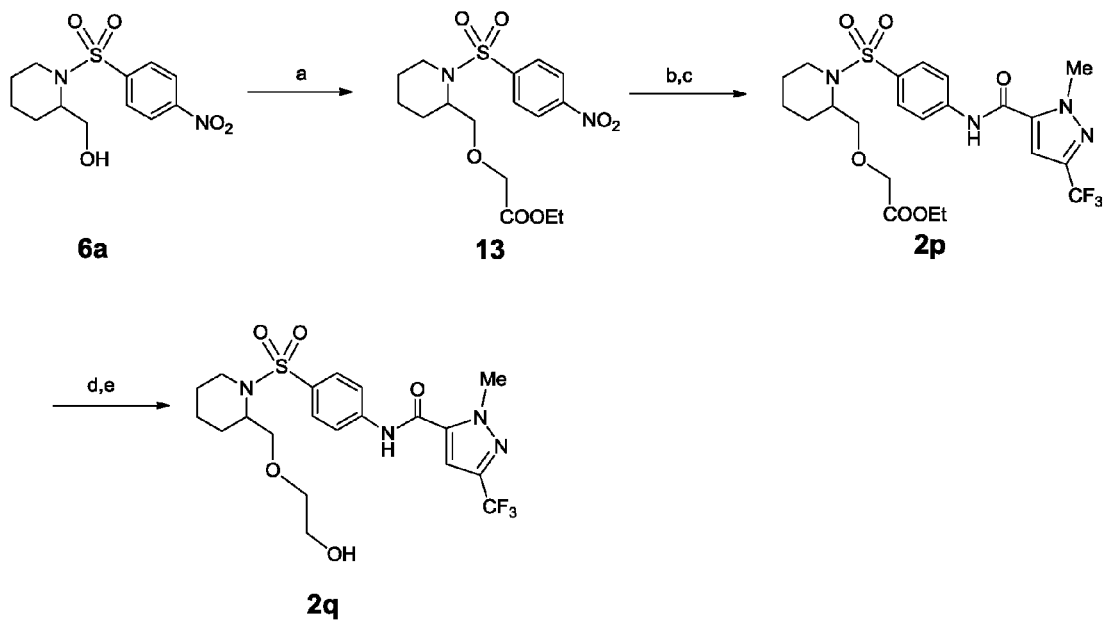
FIG. 5 illustrates preparation of embodiments of the disclosure. $Rh_2OAc_4$, $CH_2Cl_2$; (b) $H_2$, Pd/C, MeOH; (c) 8, i$Pr_2NEt$, $CH_2Cl_2$; (d) NaOH, THF/H2O; (e) BOP, i$Pr_2NEt$, THF, $NaBH_4$; (f) KOH, DMSO, MeI.

The synthesis of 2p was initiated by addition of a rhodium carbenoid across the hydroxylic bond, to form an ether bond. Thus, decomposition of ethyl diazoacetate in the presence of Rh2OAc4 generated a carbenoid that inserted across the OH bond to give 13. Reduction of the nitro group of 13 followed by coupling with 8 afforded analog 2p, which on hydrolysis of the ester and BOP/NaBH4 mediated reduction of the resultant carboxylic acid, provided 2q (FIG. 5).

Figure 6:
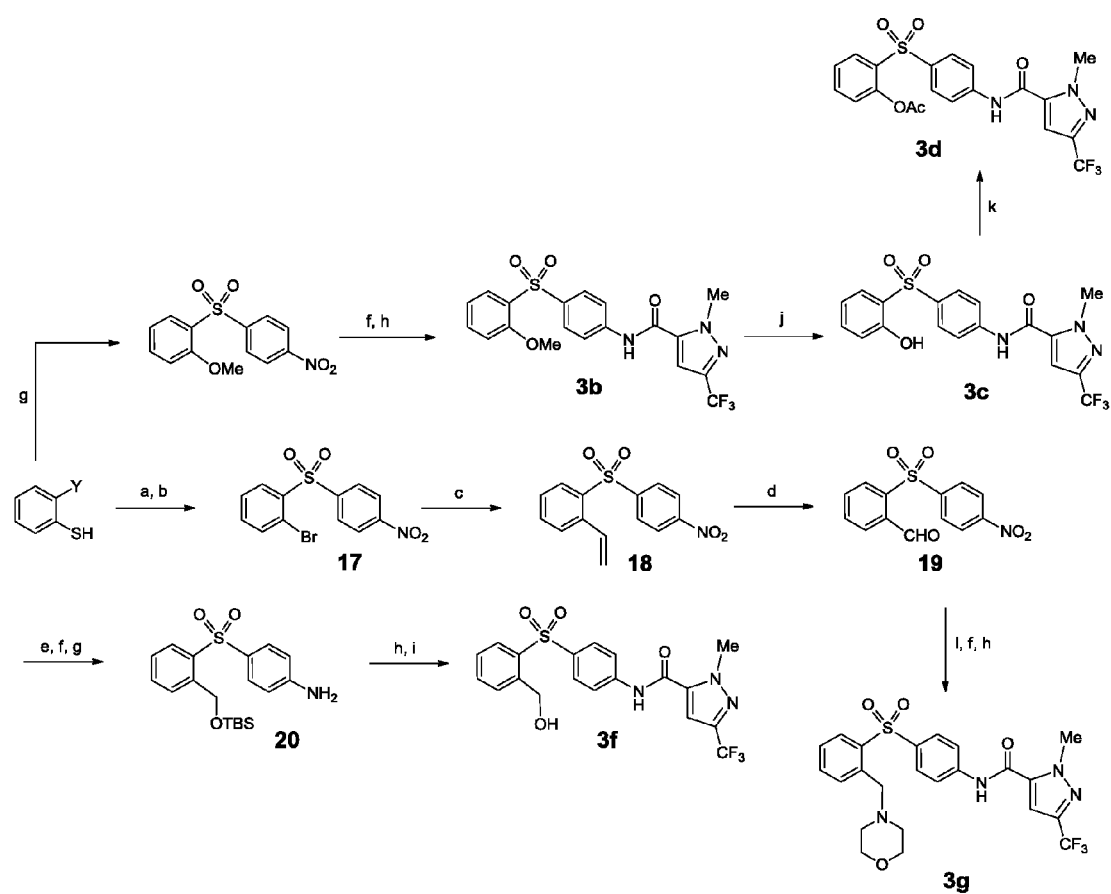
FIG. 6 illustrates preparation of embodiments of the disclosure. (a) 1-fluoro-4-nitrobenzene, $Na_2CO_3$, EtOH, 80° C.; (b) mCPBA, $CH_2Cl_2$; (c) tributyl(vinyl)tin, $Pd(PPh_3)_4$, THF, 80° C.; (d) $OsO_4$, $NaIO_4$, THF/$H_2O$; (e) DIBAL-H, THF; (f) $SnCl_2$, $CH_2Cl_2$/MeOH; (g) TBSCl, imidazole, DMF; (h) 8, i-$Pr_2NEt$, $CH_2Cl_2$; (i) TBAF, THF; (j) $BBr_3$, $CH_2Cl_2$; (k) AcCl, THF; (l) morpholine, $NaBH(OAc)_3$, $CH_2Cl_2$.

Replacement of the piperidine ring with phenyl or substituted phenyl via the general route shown in FIG. 6 was also explored. Unsubstituted phenyl gave analog 3a. The latter was found to be as active as compound 1 (AS-136a) triggering an SAR study of the series (Table 2). Coupling of 2-bromothiophenol 16a with 1-fluoro-4-nitrobenzene followed by oxidation of sulfur using MCPBA gave sulfone 17. Reduction of the nitro group of 17, followed by coupling with acid chloride 8 gave analog 3b. Substituting starting thiol 16a with 2-methoxythiophenol 16b, followed by the same sequence delivered analog 3b. Demethylation of 3b with $BBr_3$ afforded phenol analog 3c, which on acylation gave analog 3d. To make additional analogs of the phenyl series, utilizing bromide 17 to append substituents was envisioned. However, attempts to lithiate bromide 17 using n-BuLi or t-BuLi were unfruitful resulting in decomposition of the bromide. Stille coupling offered an alternative. When 17 was treated with tributyl(vinyl)tin in the presence of $Pd(PPh_3)_4$, the desired coupling product 18 was obtained in a decent yield. Reduction of the nitro group followed by coupling with acid chloride 8 afforded analog 3e (FIG. 6 and Table 2). Subjecting olefin 18 to osmium tetroxide-mediated oxidative cleavage of the double bond gave aldehyde 19, a compound utilized in the synthesis of additional analogs. Reduction of the aldehyde, $SnCl_2$ reduction of the nitro group and protection of the alcohol as a silyl ether gave aniline 20. Coupling of 20 with acid chloride 8 followed by cleavage of the silyl group furnished analog 3f. Aldehyde 19 was also used for the synthesis of morpholine 3g by means of reductive-amination, followed by reduction of the nitro group and coupling with acetyl chloride 8 (FIG. 6).

Combination Therapies

In certain embodiments, the pharmaceutical composition comprising a compound disclosed herein is administered in combination with one or more second antiviral agent such as is abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, and/or zidovudine.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

EXPERIMENTAL

Example 1

Compound Preparation and Characterization

See FIGS. 2-6.

Compound 1a; $^1$H NMR (CHLOROFORM-d, 400 MHz): δ 8.17 (s, 1H), 7.74-7.79 (m, 2H), 7.64-7.69 (m, 2H), 7.06 (s, 1H), 4.51 (s, 2H), 4.19-4.28 (m, 4H), 3.76-3.68 (m, 1H), 3.54-3.65 (m, 2H), 3.27 (s, 3H), 3.03-2.94 (m, 1H), 1.76-1.70 (m, 1H), 1.42-1.60 (m, 4H), 1.20-1.37 (m, 1H). Anal. calcd for $C_{21}H_{29}F_3N_4O_5S$: C, 49.79; H, 5.77; N, 11.06. Found: C, 49.07; H, 5.06; N, 11.31.

Compound 1b; $^1$H NMR (CHLOROFORM-d, 400 MHz): δ 8.09 (s, 1H), 7.69-7.78 (m, 4H), 7.03 (s, 1H), 4.56 (s, 2H), 4.25 (s, 3H), 3.78 (d, J=11.7 Hz, 2H), 3.30-3.38 (m, 5H), 2.27 (td, J=2.3, 11.9 Hz, 2H), 1.72-1.83 (m, 2H), 1.50 (m, 1H), 1.29-1.42 (m, 2H).

Compound 1c; $^1$H NMR (CHLOROFORM-d, 400 MHz): δ 7.97 (s, 1H), 7.71-7.77 (m, 4H), 7.01 (s, 1H), 4.56 (s, 2H), 4.26 (s, 3H), 3.79 (d, J=11.3 Hz, 2H), 3.30-3.38 (m, 5H), 2.27 (td, J=2.5, 11.8 Hz, 2H), 1.79 (d, J=10.6 Hz, 2H), 1.45-1.56 (m, 1H), 1.35 (m, 2H). Anal. calcd for $C_{21}H_{29}F_3N_4O_5S$: C, 49.79; H, 5.77; N, 11.06. Found: C, 49.17; H, 5.09; N, 11.21.

Compound 2b; $^1$H NMR (CHLOROFORM-d, 400 MHz): δ 8.03 (s, 1H), 7.83-7.89 (m, 2H), 7.67-7.72 (m, 2H), 7.02 (s, 1H), 4.26 (s, 3H), 4.21 (br. s., 1H), 3.64 (m, 5H), 2.88-2.97 (m, 1H), 2.38-2.51 (m, 6H), 1.77 (m, 1H), 1.41-1.58 (m, 4H), 1.31 (m, 1H). Anal. calcd for $C_{22}H_{28}F_3N_5O_4S$: C, 51.25; H, 5.47; N, 13.58. Found: C, 51.05; H, 5.45; N, 13.42.

Compound 2c; $^1$H NMR (CHLOROFORM-d, 400 MHz): δ 7.93 (s, 1H), 7.80-7.86 (m, 2H), 7.69-7.75 (m, 2H), 6.99 (s, 1H), 4.26 (s, 3H), 4.16 (m, 1H), 3.79 (d, J=13.3 Hz, 1H), 3.51 (dd, J=7.2, 12.3 Hz, 1H), 3.30-3.38 (m, 1H), 2.92-3.02 (m, 1H), 1.65-1.71 (m, 1H), 1.53-1.62 (m, 5H).

Compound 2d; $^1$H NMR (CHLOROFORM-d, 400 MHz): δ 8.27 (s, 1H), 7.77-7.83 (m, 2H), 7.68-7.75 (m, 2H), 7.03 (s, 1H), 4.25 (s, 3H), 3.87-3.96 (m, 1H), 3.77 (d, J=11.0 Hz, 1H), 2.92-3.06 (m, 2H), 2.64 (dd, J=5.7, 13.5 Hz, 1H), 1.28-1.60 (m, 6H).

Compound 2e; $^1$H NMR (CHLOROFORM-d, 400 MHz): δ 9.31 (s, 1H), 7.83-7.90 (m, 2H), 7.76-7.82 (m, 2H), 7.22 (s, 1H), 6.08 (t, J=5.5 Hz, 1H), 4.26 (s, 3H), 4.03-4.13 (m, 1H), 3.67-3.77 (m, 1H), 3.56 (ddd, J=5.3, 10.9, 14.0 Hz, 1H), 3.20-3.28 (m, 1H), 3.02-3.11 (m, 1H), 2.0 (m, 3H), 1.38-1.53 (m, 4H), 1.20-1.34 (m, 1H). Anal. calcd for $C_{20}H_{25}F_3N_4O_4S$: C, 49.28; H, 4.96; N, 14.37. Found: C, 49.02; H, 4.98; N, 14.08.

Compound 2g; $^1$H NMR (CHLOROFORM-d, 400 MHz): δ 8.19 (s, 1H), 7.69-7.78 (m, 4H), 7.03 (s, 1H), 6.75 (dd, J=4.0, 16.0 Hz, 1H), 5.89 (dd, J=2.0, 16.0 Hz, 1H), 4.69 (br. s., 1H), 4.25 (s, 3H), 4.15 (q, J=7.0 Hz, 2H), 3.67 (d, J=12.9 Hz, 1H), 2.95-3.05 (m, 1H), 1.63-1.78 (m, 2H), 1.56 (d, J=11.0 Hz, 7H), 1.32-1.47 (m, 7H), 1.25 (t, J=8.0 Hz, 3H). Anal. calcd for $C_{22}H_{25}F_3N_4O_5S$: C, 51.36; H, 4.90; N, 10.89. Found: C, 51.36; H, 4.90; N, 10.89. Found: C, 51.42; H, 4.90; N, 10.79.

Compound 2h; $^1$H NMR (CHLOROFORM-d, 400 MHz): δ 8.32 (s, 1H), 7.63-7.77 (m, 4H), 7.05-7.10 (m, 1H), 5.63-5.72 (m, 1H), 5.52-5.61 (m, 1H), 4.54 (br. s., 1H), 4.24 (s, 3H), 3.95-4.08 (m, 2H), 3.64 (d, J=12.5 Hz, 1H), 3.47 (d, J=5.1 Hz, 1H), 2.91-3.02 (m, 1H), 1.81 (t, J=5.9 Hz, 1H), 1.34-1.74 (m, 6H). Anal. calcd for $C_{20}H_{23}F_3N_4O_4S$: C, 50.84; H, 4.91; N, 11.86. Found: C, 50.57; H, 4.98; N, 11.63.

Compound 2i; $^1$H NMR (CHLOROFORM-d, 400 MHz): δ 8.34 (s, 1H), 7.66-7.83 (m, 4H), 7.07 (s, 1H), 4.25 (s, 3H), 4.02 (s, 1H), 3.73 (d, J=14.5 Hz, 1H), 3.63 (m, 2H), 2.93-3.05 (m, 1H), 2.16 (s, 3H), 1.59-1.81 (m, 2H), 1.28-1.59 (m, 6H). Anal. calcd for $C_{20}H_{25}F_3N_4O_4S$: C, 50.62; H, 5.31; N, 11.81. Found: C, 50.35; H, 5.28; N, 11.62.

Compound 2j; $^1$H NMR (CHLOROFORM-d, 400 MHz): δ 8.26 (s, 1H), 7.67-7.79 (m, 4H), 7.06 (s, 1H), 4.25 (s, 3H), 4.11 (q, J=7.0 Hz, 2H), 3.99-4.07 (m, 1H), 3.74 (d, J=14.5 Hz, 1H), 2.96-3.07 (m, 1H), 2.36 (t, J=7.4 Hz, 2H), 2.00-2.13 (m, 1H), 1.60-1.72 (m, 1H), 1.30-1.55 (m, 5H), 1.24 (t, J=7.2 Hz, 3H), 1.01-1.17 (m, 1H).

Compound 2l, 2m, 2k; $^1$H NMR (CHLOROFORM-d, 400 MHz): δ 8.00 (s, 1H), 7.86 (d, J=8.6 Hz, 2H), 7.75 (d, J=8.6 Hz, 2H), 6.99 (s, 1H), 4.26 (s, 3H), 4.17-4.25 (m, 1H), 3.90 (d, J=14.1 Hz, 1H), 3.74-3.83 (m, 1H), 3.67 (d, J=5.1 Hz, 1H), 2.97-3.06 (m, 1H), 2.84 (dd, J=4.9, 8.4 Hz, 1H), 1.93-2.02 (m, 1H), 1.40-1.54 (m, 5H), 1.32-1.40 (M, 1H).

Compound 2o; $^1$H NMR (CHLOROFORM-d, 400 MHz): δ 8.18 (s, 1H), 7.74-7.80 (m, 2H), 7.65-7.72 (m, 2H), 7.05 (s, 1H), 4.25 (s, 3H), 4.04-4.11 (m, 1H), 3.76 (dd, J=4.1, 14.3 Hz, 1H), 3.67 (t, J=4.5 Hz, 1H), 2.97-3.08 (m, 1H), 2.23-2.45 (m, 6H), 1.78-1.90 (m, 1H), 1.55-1.66 (m, 1H), 1.30-1.53 (m, 5H).

Compound 2q; $^1$H NMR (CHLOROFORM-d, 400 MHz): δ 8.14 (s, 1H), 7.77-7.83 (m, 2H), 7.65-7.70 (m, 2H), 7.02-7.06 (m, 1H), 4.25 (s, 3H), 4.14-4.23 (m, 3H), 3.99 (d, J=3.1 Hz, 2H), 3.73 (d, J=14.1 Hz, 1H), 3.60-3.67 (m, 2H), 2.96-3.06 (m, 1H), 1.77 (d, J=12.9 Hz, 1H), 1.37-1.56 (m, 3H), 1.26 (t, J=8.0 Hz, 3H).

Compound 2r; $^1$H NMR (CHLOROFORM-d, 400 MHz): δ 8.73 (s, 1H), 7.70-7.83 (m, 4H), 7.11 (s, 1H), 4.30-4.39 (m, 1H), 4.25 (s, 3H), 3.72 (t, J=9.4 Hz, 2H), 3.58-3.68 (m, 2H), 3.45-3.54 (m, 2H), 3.40 (d, J=10.6 Hz, 1H), 3.25 (br. s., 1H), 2.98 (td, J=2.5, 13.2 Hz, 1H), 1.63-1.74 (m, 2H), 1.35-1.63 (m, 3H). Anal. calcd for $C_{20}H_{25}F_3N_4O_5S$: C, 48.97; H, 5.14; N, 11.42. Found: C, 48.94; H, 5.08; N, 11.26.

Compound 4e; $^1$H NMR (CHLOROFORM-d, 400 MHz): δ 7.93 (s, 1H), 7.79-7.84 (m, 2H), 7.71 (d, J=8.6 Hz, 2H), 6.99 (s, 1H), 4.90 (s, 1H), 4.86 (s, 1H), 4.26 (s, 3H), 3.74 (s, 2H), 3.60-3.66 (m, 4H), 3.20 (t, J=7.2 Hz, 2H), 2.47 (t, J=7.2 Hz, 2H), 2.35-2.41 (m, 4H), 1.70 (s, 3H).

Compound 4f; Anal. cacld for $C_{25}H_{28}F_3N_5O_4$: C, 54.44; H, 5.12; N, 12.70. Found: C, 54.38; H, 5.20; N, 12.55.

Compound 4d; $^1$H NMR (CHLOROFORM-d, 400 MHz): δ 7.99 (s, 1H), 7.79-7.84 (m, 2H), 7.69-7.75 (m, 2H), 7.00 (s, 1H), 5.58-5.70 (m, 1H), 5.13-5.20 (m, 2H), 4.26 (s, 3H), 3.86 (d, J=6.3 Hz, 2H), 3.62-3.69 (m, 4H), 3.24 (t, J=7.0 Hz, 2H), 2.51 (t, J=7.0 Hz, 2H), 2.38-2.44 (m, 4H).

Compound 4c; $^1$H NMR (CHLOROFORM-d, 400 MHz): δ 8.20 (s, 1H), 7.75-7.81 (m, 2H), 7.68-7.74 (m, 2H), 7.03 (s, 1H), 4.25 (s, 3H), 3.61-3.69 (m, 4H), 3.15-3.23 (m, 2H), 2.85-2.97 (m, 3H), 2.47-2.55 (m, 3H), 2.37-2.46 (m, 4H), 1.81-1.92 (m, 1H), 1.64 (s, 2H), 0.90 (d, J=6.7 Hz, 6H).

Compound 4b; $^1$H NMR (CHLOROFORM-d, 400 MHz): δ 8.13 (s, 1H), 7.76-7.81 (m, 2H), 7.68-7.73 (m, 2H), 7.02 (s, 1H), 4.25 (s, 3H), 3.61-3.71 (m, 4H), 3.19-3.27 (m, 2H), 3.06-3.14 (m, 2H), 2.48-2.55 (m, 2H), 2.39-2.47 (m, 4H), 1.63 (s, 2H), 1.50-1.59 (m, 2H), 0.86 (t, J=7.4 Hz, 3H). Anal. calcd for $C_{21}H_{28}F_3N_5O_4S$: C, 50.09; H, 5.60; N, 13.91. Found: C, 50.16; H, 5.60; N, 13.76.

Compound 4a; $^1$H NMR (CHLOROFORM-d, 400 MHz): δ 8.03 (s, 1H), 7.70-7.81 (m, 4H), 7.01 (s, 1H), 4.25 (s, 3H), 3.64-3.71 (m, 4H), 3.15 (t, J=6.8 Hz, 2H), 2.80 (s, 3H), 2.53 (t, J=6.8 Hz, 2H), 2.42-2.48 (m, 4H).

Compound 3a; $^1$H NMR (CHLOROFORM-d, 400 MHz): δ 8.10 (s, 1H), 7.85-7.93 (m, 4H), 7.69-7.75 (m, 2H), 7.53-7.59 (m, 1H), 7.46-7.53 (m, 2H), 7.03 (s, 1H), 4.22 (s, 3H). Anal. calcd for $C_{18}H_{14}F_3N_3O_3S$: C, 52.81; H, 3.45; N, 10.26. Found: C, 52.31; H, 3.41; N, 9.95.

Compound 3b; $^1$H NMR (CHLOROFORM-d, 400 MHz): δ 8.11 (dd, J=1.8, 8.0 Hz, 1H), 8.04 (s, 1H), 7.90-7.95 (m, 2H), 7.66-7.71 (m, 2H), 7.51-7.57 (m, 1H), 7.07-7.13 (m, 1H), 7.02 (s, 1H), 6.87-6.91 (m, 1H), 4.24 (s, 3H), 3.76 (s, 3H).

Compound 3c; $^1$H NMR (CHLOROFORM-d, 400 MHz): δ 7.86-7.92 (m, 2H), 7.77-7.82 (m, 2H), 7.65 (dd, J=1.6, 8.2 Hz, 1H), 7.37-7.43 (m, 1H), 7.11 (s, 1H), 6.90-6.96 (m, 2H), 4.20 (s, 3H). Anal. calcd for $C_{18}H_{14}F_3N_3O_4S$: C, 50.82; H, 3.32; N, 9.88. Found: C, 50.67; H, 3.29; N, 9.61.

Compound 3d; $^1$H NMR (400 MHz, CHLOROFORM-d) δ 8.14 (dd, J=1.76, 8.02 Hz, 1H), 7.87-7.93 (m, 3H), 7.70-7.76 (m, 2H), 7.58-7.63 (m, 1H), 7.41 (dt, J=1.17, 7.83 Hz, 1H), 7.14 (dd, J=0.98, 8.02 Hz, 1H), 6.96 (s, 1H), 4.24 (s, 3H), 2.32 (s, 3H). Anal. calcd for $C_{20}H_{16}F_3N_3O_5S$: C, 51.39; H, 3.45; N, 8.99. Found: C, 51.31; H, 3.32; N, 8.80.

Compound 3e; $^1$H NMR (400 MHz, CHLOROFORM-d) δ 8.12-8.17 (m, 1H), 8.08 (s, 1H), 7.76-7.83 (m, 2H), 7.65-7.71 (m, 2H), 7.51-7.59 (m, 2H), 7.41-7.50 (m, 2H), 7.02 (s, 1H), 5.52 (dd, J=1.17, 17.22 Hz, 1H), 5.33 (dd, J=0.78, 10.96 Hz, 1H), 4.22 (s, 3H). Anal. calcd for $C_{20}H_{16}F_3N_3O_3S$: C, 55.17; H, 3.70; N, 9.65. Found: C, 54.99; H, 3.60; N, 9.64.

Compound 3f; $^1$H NMR (400 MHz, CHLOROFORM-d) δ 8.10 (dd, J=1.17, 7.83 Hz, 1H), 8.00 (s, 1H), 7.84-7.90 (m, 2H), 7.71-7.77 (m, 2H), 7.59-7.65 (m, 1H), 7.48-7.57 (m, 2H), 6.98 (s, 1H), 4.73 (d, J=6.26 Hz, 2H), 4.23 (s, 3H). Anal. calcd for $C_{19}H_{16}F_3N_3O_4S$: C, 51.93; H, 3.67; N, 9.56. Found: C, 52.01; H, 3.53; N, 9.40.

Compound 3g; $^1$H NMR (CHLOROFORM-d, 400 MHz): δ 8.16 (dd, J=1.2, 7.8 Hz, 1H), 7.99 (s, 1H), 7.83-7.89 (m, 2H), 7.68-7.74 (m, 3H), 7.54-7.60 (m, 1H), 7.42-7.48 (m, 1H), 7.01 (s, 1H), 4.24 (s, 3H), 3.77 (s, 2H), 3.50-3.57 (m, 4H), 2.27 (m, 4H). Anal. calcd for $C_{23}H_{23}F_3N_4O_4S$: C, 54.32; H, 4.56; N, 11.02. Found: C, 54.36; H, 4.42; N, 10.85.

Example 2

Viral CPE-Reduction Assay and Virus Yield Reduction Assay

Methods for evaluating viral activity are provided for in Yoon et al., J Biomol Screen., 2008, 13(7): 591-608 and Krumm et al., PLoS ONE, 2011, 6(5), e20069, both hereby incorporated by reference in their entirety. In certain instances, Vero-SLAM cells were infected with MeV-Alaska in four replicates per compound concentration in a 96-well plate format at an MOI of 0.4 pfu/cell in the presence of the inhibitor. At 96 hours post-infection, cell monolayers were subjected to crystal violet staining (0.1% crystal violet in 20% ethanol), and the absorbance of dried plates at 560 nm determined. Virus-induced cytopathicity was then calculated according to the formula [% rel. CPE=100−(experimental−minimum)/(maximum−minimum)*100], with minimum referring to infected, vehicle-treated wells and maximum to mock-infected wells.

To assess viral resistance to inhibition based on reduction of titers of infectious particles, 2×10$^5$ cells per well were infected in a 12-well plate format with the specified myxovirus at an MOI=0.1 pfu/cell (all paramyxoviruses assessed) or 0.05 pfu/cells (influenza viruses) in the presence of a range of compound concentrations as indicated or equivalent volumes of solvent (DMSO) only, and incubated in the presence of compound at 37° C. When vehicle treated controls approached the end of the logarithmical growth phase (typically 28-36 hours postinfection depending on the virus assessed), progeny viral particles were harvested and tittered by TCID50 titration, plaque assay or TaqMan real-time PCR, respectively. Plotting virus titers as a function of compound concentration allowed quantitative assessment of resistance. Where applicable, 50% inhibitory concentrations were calculated using the variable slope (four parameters) non-linear regression-fitting algorithm embedded in the Prism 5 software package (GraphPad Software).

Figure 9:
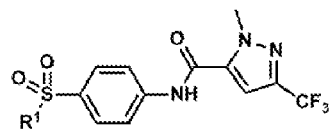
FIG. 9 shows data for inhibition for certain embodiments of the disclosure. aEC50 (CPE assay, MV alaska) in micromolar (mM) as an average of three experiments.

The 2-position of the piperidine (Table 1) were generally found to yield more active compounds compared to the 3- or 4-position (FIG. 9). The MOM ether analogs (1a-c) demonstrate a trend whereby substitution at C-2 of the piperidine is favored. The 2-piperidine 1a is 2-fold more potent than the corresponding 3-piperidine, while the 4-substituted derivatives reduce activity by almost 10-fold (1a, 1b and 1c, Table 1, FIG. 9). Morpholine derivatives (2b and 2n) showed potency. Esters 2g and 2i were found to be 2-fold more active by comparison with the corresponding alcohols (2h and 2j, Table 1). S-chirality is typically more active over R— as demonstrated by the 3-fold loss of activity for 2l compared to 2m.

TABLE 1
MeV antiviral action (CPE) of the piperidine series of analogs, (EC$_{50}$).
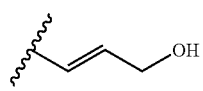 [SMILES: */C=C/CO]
| Comp. | R | EC$_{50}$ (μM) (MV-Alaska) (CPE inhib.) | Comp. | R | EC$_{50}$ (μM) (MV-Alaska) (CPE inhib.) |
|---|---|---|---|---|---|
| AS-136a | —H | 2.0 | 2h | 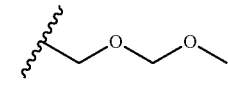 [SMILES: *COCOC] | 6.8 |
| 1a | 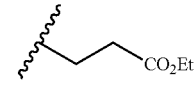 | 1.5 | 2i | 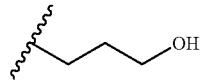 | 2.7 |
| 1b | n/a | 3.8 | 2j | 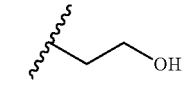 | 6.7 |
| 1c | n/a | 16.0 | 2k | 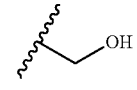 | 2.7 |
| 2a | 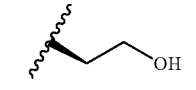 | 2.8 | 2l | 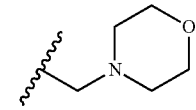 | 8.3 |
| 2b | 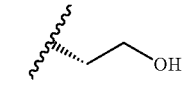 | 9.3 | 2m | 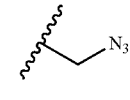 | 3.1 |
| 2c | 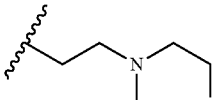 | 1.5 | 2n | 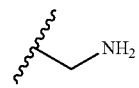 | 4.6 |
| 2d | 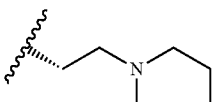 | 55.0 | 2o | 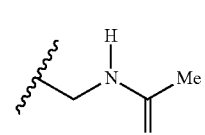 | 4.5 |
| 2e | 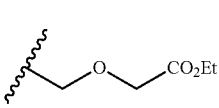 [SMILES: *COCC(=O)OCC] | 14.0 | 2p | | 25.0 |

TABLE 1-continued

MeV antiviral action (CPE) of the piperidine series of analogs, (EC$_{50}$).

| Comp. | R | EC$_{50}$ (μM) (MV-Alaska) (CPE inhib.) | Comp. | R | EC$_{50}$ (μM) (MV-Alaska) (CPE inhib.) |
|---|---|---|---|---|---|
| 2f | —CH$_2$N(CH$_3$)$_2$ | >150.0 | 2q | —CH$_2$OCH$_2$CH$_2$OH | 8.3 |
| 2g | —CH=CHCO$_2$Et | 3.7 | | | |

TABLE 2

MeV antiviral action (CPE) of the phenyl and acyclic series of analogs, (EC50).

| Compd. | R$_2$ | EC$_{50}$ (μM) (MV-Alaska) (CPE inhibition) |
|---|---|---|
| 3a | —H | 2.8 |
| 3b | —OCH$_3$ | 3.1 |
| 3c | —OH | 4.5 |
| 3d | —OAc | 4.5 |
| 3e | —CH=CH$_2$ | >50.0 |
| 3f | —CH$_2$OH | 3.1 |
| 3g | —CH$_2$-morpholine | >75.0 |

For the phenyl series, analog 3a is as active and its activity is comparable to that of methoxy 3b and alcohol 3f (Table 3). SAR suggests a hydrophobic environment on the target protein housing the left part of our molecules disfavoring hydrogen bonding. Since poor solubility was thought to contribute to low oral bioavailability for AS-136a, the aqueous solubility was measured for some of the more potent derivatives via nephylometry (buffer, pH=7.4, Table 3).

TABLE 3

Aqueous solubility, virus yields (EC$_{50}$) and toxicity (CC$_{50}$) for selected compounds.

| Entry ID | Aqueous solubility (μg/ml) Test[a] | EC$_{50}$ (μM) (MV-Alaska) | | CC$_{50}$(μM) (Vero cells) (MTT cytocoxicity)[d] |
|---|---|---|---|---|
| | | CPE inhibition[b] | virus titer reduction[c] | |
| AS-136a | <15 | 2.0 | 0.014 | >75 |
| 2a | 61 | 2.3 | 0.85 ± 0.050 | >75 |
| 2k | 62 | 2.7 | 0.060 | >75 |
| 2n | 55 | 4.6 | | >75 |
| 2o | 60 | 4.5 | 0.020 | >75 |
| 3a | 22 | 2.8 | 0.020 | >75 |
| 3b | <15 | 3.1 | | >75 |
| 3c | 67 | 4.5 | | 75 |
| 3f | 46 | 3.1 | | >75 |

[a]solubility data generated through Nephelometer using standard procedure;

[b]EC$_{50}$ not determined (ND) when CC50 ≤15 μM. Values represent averages of four experiments ± SD; highest concentration assessed 75 μM, lowest concentration assessed 2.3 μM;

[c]Determined only when CPE inhibition-based EC$_{50}$ concentration <3.0 μM. Values represent averages of two to four experiments ± SEM; highest concentration assessed 1 μM;

[d]Values represent averages of at least three experiments ± SD; highest concentration assessed 75 μM.

AS-136a and phenyl analog 3a show solubility with values at 15.0 μg/ml and 22 μg/ml, respectively. The alcohol analogs 2a and 2k both deliver improved solubility with measured values at 61 and 62 μg/ml, respectively. To our great delight, the morpholine analog 2n also furnish similar solubility compared with the corresponding free alcohol derivative 2k. Compounds with moderate solubility (~60 μg/ml) and good potency (<5.0 μM) in the CPE assay were further tested with the virus titer reduction assay. Primary alcohol derivative 2k (EC$_{50}$=2.7 μM, CPE assay; solubility 62 μg/ml) delivers an EC50 of 60 nM in the virus titer reduction assay (2k; Table 3). Replacement of the hydroxyl group with morpholine led to analog 2o with an $EC_{50}$ value of 20 nM in the virus titer assay and solubility around 60 µg/ml (2o; Table 3).

Example 2

Figure 7:
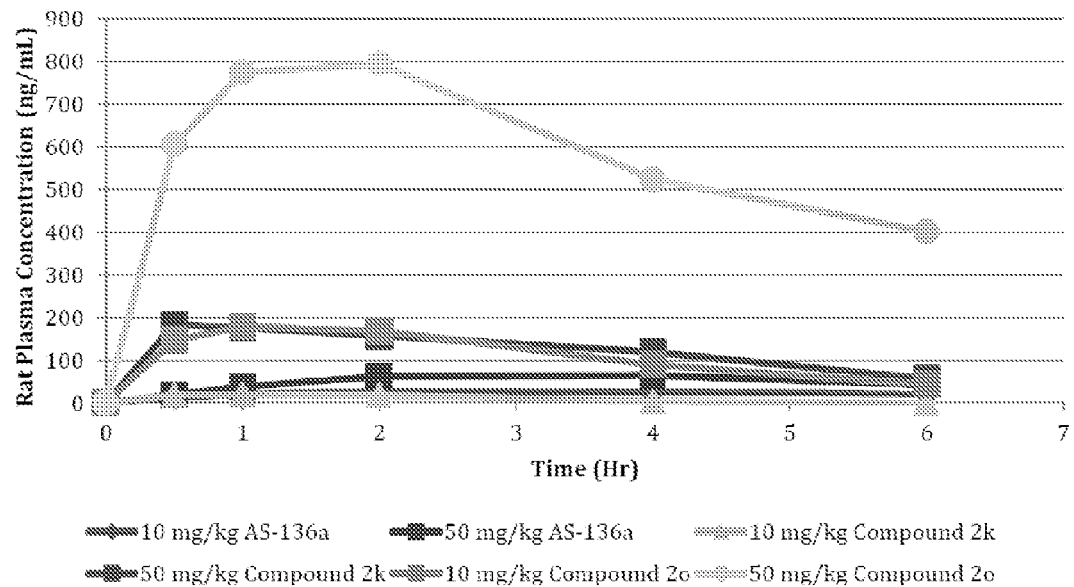
FIG. 7 shows data on the rat plasma concentration following p.o. dosing by oral gavage. Preliminary pharmacokinetic (PK) studies in the Sprague-Dawley rat compared AS-136a with compounds 2k and 2o following p.o. dosing by oral gavage at 10 mg/kg and 50 mg/kg in a PEG200/0.5% methylcellulose (10/90) vehicle (n=4/group).
Figure 8:
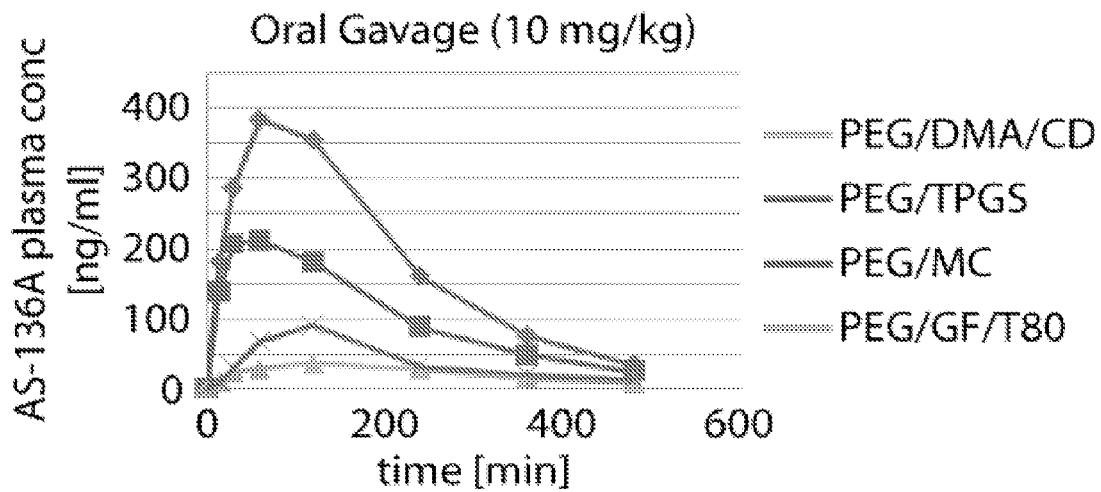
FIG. 8 shows data on plasma concentrations in SD rats after p.o. dosing in various vehicle formulations. PEG/DMA/CD is polyethyleneglycol-dimethacrylate-cyclodextrin blend (PEG-DMA-CD); PEG/TPGS is alpha-tocopheryl succinate esterified to polyethylene glycol; PEG/MC is polyethyleneglycol-methylcellulose.

Hydroxyl (2k) and Morpholinyl (2o) Moieties and AS-136a in a Pharmacokinetic (PK) Study Comparisons of 2k, 2o, and AS-136a are provided in FIG. 7, and the various PK parameters are listed in Table 4. The data from the preliminary pharmacokinetic studies using the 6-hour time point are reported for comparison purposes. Compound 2o shows a 10-fold exposure (AUC/Cmax) increase in rat relative to AS-136a and displays near dose proportionality in the range of 10 mg/kg to 50 mg/kg. In contrast, the primary alcohol analog 2k reveals a reasonable Cmax and AUC at 50 mg/kg dosing, but it has poor plasma concentration in rat and non-proportionality presumably due to high first-pass metabolism of the primary alcohol. On the basis of its excellent in vitro potency, good solubility and pharmacokinetic profile, compound 2o was chosen for further bioavailability evaluation. The compound was dosed at 2 mg/kg i.v. and 10 mg/kg p.o. in rat and exhibits oral bioavailability (F=39%).

TABLE 4

PK Profile for Compounds AS-136a, 2k and 2o

| cmpd | oral dose (mg/kg)[a] | $T_{max}$ (hr) | Cmax (ng/mL)[b] | T½ (hr)[b] | AUC (0-t) (hr * ng/ mL)[b] | AUC (0-∞) (hr * ng/ mL)[b] |
|---|---|---|---|---|---|---|
| AS-136a | 10 | 2.5 | 26.9 | 12.7 | 132 | 513 |
| AS-136a | 50 | 2.7 | 72.2 | 3.7 | 308 | 483 |
| 2k | 10 | 1 | 19.8 | 0.8 | 56.3 | 56.8 |
| 2k | 50 | 0.5 | 184 | 2.7 | 754 | 973 |
| 2o | 10 | 1.1 | 195 | 2.2 | 683 | 818 |
| 2o | 50 | 1.5 | 823 | 6.5 | 3521 | 7860 |

[a]Sprague-Dawley rat dosed at 10 mg/kg and 50 mg/kg as a suspension in PEG200/0.5% methylcellulose (10/90) formulation, respectively. n = 4 animals per study.
[b]Estimation of PK parameters by non-compartmental analysis of these data, which was accomplished using standard PK software (WinNonlin 5.3, Pharsight ®).

The invention claimed is:

1. A pharmaceutical composition comprising a compound of Formula I and dimethacrylated cyclodextrin and optionally polyethylene glycol, wherein

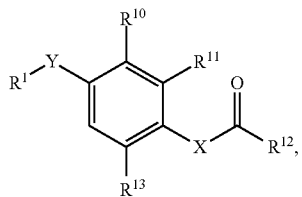

Formula I or salts thereof wherein,

X is O, S, NH, or $CH_2$;

Y is $SO_2$ or SO;

$R^1$ is dialkylamino, aryl, or heterocyclyl, optionally substituted with one or more, the same or different, $R^{14}$;

$R^{12}$ is 1,3-dimethyl-pyrazol-5-yl optionally substituted with one or more, the same or different, halogen on the methyl groups of the pyrazole ring;

$R^{10}$, $R^{11}$, and $R^{13}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein each $R^{10}$, $R^{11}$, and $R^{13}$ are optionally substituted with one or more, the same or different, $R^{14}$;

$R^{14}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{14}$ is optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, N-methylsulfamoyl, N-ethylsulfamoyl, N,N-dimethyl sulfamoyl, N,N-diethylsulfamoyl, N-methyl-N-ethylsulfamoyl, carbocyclyl, aryl, or heterocyclyl.

2. A compound (S)-1-methyl-N-(4-((2-(2-morpholinoethyl)piperidin-1-yl)sulfonyl)phenyl)-3-(trifluoromethyl)-1H-pyrazole-5-carboxamide or salt thereof.

3. A pharmaceutical composition comprising a compound as provided in claim 2 and a pharmaceutically acceptable excipient.

4. A method of treating a measles viral infection comprising administering an effective amount of a pharmaceutical composition of claim 3 to a subject in need thereof.

* * * * *